(12) United States Patent
Inch (10) Patent No.: US 11,712,362 B2
(45) Date of Patent: Aug. 1, 2023

(54) DEVICE FOR STOMA BAG AND IMPROVED STOMA FLANGE

(71) Applicant: Anne Inch, Larkhall (GB)

(72) Inventor: Anne Hocknull Inch, Larkhall (GB)

( * ) Notice: Subject to any disclaimer, the term of this patent is extended or adjusted under 35 U.S.C. 154(b) by 167 days.

(21) Appl. No.: 17/048,593

(22) PCT Filed: Apr. 23, 2019

(86) PCT No.: PCT/GB2019/051117
§ 371 (c)(1),
(2) Date: Oct. 17, 2020

(87) PCT Pub. No.: WO2019/202337
PCT Pub. Date: Oct. 24, 2019

(65) Prior Publication Data
US 2021/0145623 A1    May 20, 2021

(30) Foreign Application Priority Data
Apr. 20, 2018    (GB) ...................................... 1806456

(51) Int. Cl.
*A61F 5/448*    (2006.01)
*A61F 5/443*    (2006.01)
*A61F 5/449*    (2006.01)

(52) U.S. Cl.
CPC .............. *A61F 5/448* (2013.01); *A61F 5/443* (2013.01); *A61F 5/449* (2013.01)

(58) Field of Classification Search
CPC .......... A61F 5/445; A61F 5/448; A61F 5/443; A61F 5/449
See application file for complete search history.

(56) References Cited

U.S. PATENT DOCUMENTS

| | | | |
|---|---|---|---|
| 4,085,752 A | 4/1978 | Canale | |
| 4,331,148 A * | 5/1982 | Steer | ........................ A61F 5/445 604/333 |
| 4,406,659 A | 9/1983 | Broida | |
| 4,681,574 A * | 7/1987 | Eastman | ................. A61F 5/443 604/344 |
| 4,865,594 A | 9/1989 | Thomas | |
| 5,013,307 A | 5/1991 | Broida | |
| 5,074,852 A | 12/1991 | Castellana | |
| (Continued) | | | |

FOREIGN PATENT DOCUMENTS

| | | |
|---|---|---|
| EP | 2642958 | 2/2013 |
| GB | 2522416 A | 7/2015 |
| (Continued) | | |

*Primary Examiner* — Susan S Su
*Assistant Examiner* — Ted Yang (57) ABSTRACT

A device for containing waste material leaking from the junction between a stoma and a stoma bag having a flange, the device comprising a flange extension member which circumferentially surrounds the stoma bag flange and wherein the flange extension member includes a pouch for holding a spare stoma bag. The flange extension member can comprise an absorbent layer and can be sealed to the user's skin at its outer edge. Additionally, the flange extension member can have a waterproof or impermeable backing layer to prevent waste material from seeping through it. The device can be included in a modified stoma bag flange and a modified stoma bag.

23 Claims, 8 Drawing Sheets

(56) References Cited

U.S. PATENT DOCUMENTS

| | | | | |
|---|---|---|---|---|
| 5,203,806 A * | 4/1993 | Broida | ............... | A61F 13/45 |
| | | | | 604/338 |
| 6,231,553 B1 * | 5/2001 | Hulett | ............... | A61F 5/441 |
| | | | | 604/332 |
| 9,750,633 B1 | 9/2017 | Follenius | | |
| 11,590,016 B1 * | 2/2023 | Kayal | ............... | A61F 5/448 |
| 2011/0238024 A1 * | 9/2011 | Smith | ............... | A61F 5/445 |
| | | | | 604/336 |
| 2013/0237943 A1 | 9/2013 | Erland | | |
| 2016/0235582 A1 * | 8/2016 | Moaven | ............ | A61F 5/443 |

FOREIGN PATENT DOCUMENTS

| | | |
|---|---|---|
| GB | 2553096 A | 8/2016 |
| WO | WO97/16141 A1 | 5/1997 |

\* cited by examiner

DEVICE FOR STOMA BAG AND IMPROVED STOMA FLANGE

TECHNICAL FIELD

The present invention related to a device for use with a stoma bag and to an improved flange for a stoma bag and to an improved stoma bag.

BACKGROUND TO THE INVENTION

A stoma (also called an "ostomy"), is a surgically created opening on the surface of the abdomen through which body waste is diverted. Many medical conditions can lead to the requirement for a stoma, including bowel cancer, diverticulitis, Crohn's disease, Multiple Sclerosis and a trauma to the abdomen. It is currently estimated that over 100,000 people in the UK have a stoma and that over 10,000 stoma operations are carried out in the UK each year. The term "ostomates" is used herein to refer to people who have a stoma.

Stomas can be created by a colostomy, an ileostomy or a urostomy. In a colostomy, the stoma is created using the colon or lower bowel, whilst in an ileostomy the opening is created using the small intestine or ileum. In both cases, faeces are diverted through the stoma and are collected in a stoma bag (also known as an ostomy bag), which is attached over the opening. In a urostomy, the opening is connected to the ureters thereby by-passing the bladder so that urine is diverted through the opening. Again, a stoma (or ostomy) bag is attached to the abdomen to collect the urine. The term "waste material" is used herein to refer to any matter being passed out from a stoma, whether urine, liquefied faeces or more solid faecal matter.

A stoma bag typically comprises a flexible bag for the collection of the waste material, which includes a waterproof or impermeable lining, together with a stoma bag flange, typically of a flexible plastic, which bears a skin-friendly adhesive. The stoma bag flange can be formed as an integral part of the stoma bag (a "one-piece" design) or can be a separate element, which is then secured to a fixing element on the bag (a "two-piece" design). The flange may have a pre-cut aperture which in use is placed over the stoma. Alternatively the flange may be marked with indicia indicating various aperture sizes, so that an aperture can be cut to the size required for the user's stoma. Errors in selecting or cutting the appropriate aperture size can lead to waste material not passing into the stoma bag correctly, but leaking out past the flange and soiling clothes or bedding in an undesirable manner.

Whilst there are a number of different bag designs and types, each rely upon a secure adhesive attachment of the stoma bag flange to the skin around the stoma to ensure that all waste material is passed into the bag, which is then emptied or changed as required. Securing the stoma bag flange correctly and achieving a full seal around the stoma is essential to avoid any leakage of waste material from the stoma. The correct attachment of the stoma bag can be difficult for people suffering from arthritis or other conditions. Further, the shape of the stoma itself and the topology of the abdomen around the stoma site can be sub-optimal for ensuring secure adhesive attachment of the flange in some ostomates.

The leakage of waste material from the stoma/stoma bag junction can be source of substantial embarrassment and stress for the majority of ostomates. In particular since there is no muscular (sphincter) control over output of waste material, an ostomate will not experience any warning prior to the filling of their stoma bag. This can lead to a sudden and urgent requirement to attend to or change the stoma bag. For many ostomates, the fear of leakage from the stoma bag and the need to always carry a change of stoma bag and required accessories (for example a disposal bag, wipes etc.) is such a significant factor that they decide to limit or reduce their social interaction or other normal activities following their stoma operation.

Several attempts have been made to reduce or minimise the possibility of leakage of waste material from the junction between the stoma and stoma bag. For instance, much effort has been expended in finding improved adhesives for attachment to the skin, by the use of different flange shapes to which the stoma bag is applied, or by the use of larger diameter stoma bag flanges. To address the issue of leakage of waste material at the junction with the stoma bag, an absorbent flange extension member can be used, for example as described in U.S. Pat. No. 5,013,307.

The term "leak" and "leakage" are used herein to reference the unwanted egress of waste material from the stoma where such waste material is not collected in the stoma bag (which is intended to capture and retain all such waste material). The flange extension member reduces the likelihood of stoma output (waste material) soiling clothes and bedding, in an environmentally friendly manner and which can also increase the confidence of ostomates that unexpected soiling will not occur. However the flange extension member does not assist the ostomate with the additional problem of having to be prepared, at short notice, to change the stoma bag.

In a first aspect, the present invention provides a device for containing waste material leaking from the junction between a stoma and a stoma bag having a flange, said device comprising a flange extension member which in use circumferentially surrounds the stoma bag flange and wherein said flange extension member includes a pouch for holding a spare stoma bag. The flange extension member will normally be made of or include an absorbent material. The absorbent material can absorb any waste products which may egress from the junction.

The pouch provides a pocket which is sized and shaped to be able to hold a spare stoma bag of the user's normal type. The pouch allows the user to have the ability to store a spare stoma bag in a manner which, in addition to being highly convenient is also extremely discrete.

The pouch can include a waterproof or impermeable layer. This prevents the contents of the pouch being soiled by any waste material which might escape from the stoma bag junction.

In one embodiment the pouch is positioned on the non-skin-facing side of the flange extension. Optionally, in this embodiment, the pouch can include an absorbent face which is use is located outwardly, i.e. facing the clothes of the user. The absorbent face will assist in preventing soiling of clothes in the event of a leak from the stoma junction.

The pouch may conveniently be sized to contain other accessories helpful in changing a stoma bag. Examples include (but are not limited to) a waste disposal bag, wipes, skin-friendly adhesive, and/or a flange extension member.

The flange extension member is preferably flexible to adapt to the contours of the user's body and can conveniently be formed from sheet material, for example from planar material. The pouch is preferable low profile so that its presence does not substantially increase the bulk of the flange extension member.

The flange extension member preferably extends beyond the area of the stoma bag flange which provides adhesion to the skin of the user.

Preferably one face of the flange extension member is absorbent. In use, the absorbent face of the flange extension member will face the skin of the user. The absorbent face of the flange extension member can absorb any liquid from the waste material, and is also soft and/or non-irritant against the skin. Additionally the absorbent face will be able to absorb any sweat produced, which will reduce chafing.

The flange extension member can comprise a sheet of absorbent material, having an absorbent face. The flange extension member can be substantially formed from a sheet of absorbent material, having an absorbent face. More preferably, however, the flange extension member is a laminate comprising a layer of absorbent material (itself preferably having an absorbent face) and a waterproof or impermeable backing layer. The waterproof or impermeable backing layer can be formed from a thin film membrane or can be a sheet of other waterproof or impermeable material (such as a plastics material). The backing layer can extend beyond the absorbent layer to provide adhesion to the skin. The pouch can optionally be formed from the same material, and orientated so that the two waterproof or impermeable layers form the interior of the pouch, i.e. these layers face each other. Optionally, the flange extension member can include activated carbon, activated charcoal or other materials able to absorb odour.

The device of the invention can be used to contain waste material leaking from the stoma bag junction, irrespective of whether the waste material is solid, semi-solid or liquid. The term "contains" is used to reference the retention of the waste material within the device. Where the waste material is of liquid or semi-liquid character and the sheet comprises an absorbent layer, the absorbent layer can at least partially absorb the liquid of the waste material. Simultaneously, the device of the invention provides the ability for the stoma bag or the flange extension member to be swopped and an equivalent fresh version.

The device can include an internal aperture which has a diameter which is smaller than the outer diameter of the stoma bag flange. The stoma bag flange will therefore overlap a portion of the device around its aperture. The device can be located between the outer (non-skin facing) face of the stoma bag flange and the inner (skin facing) face of the stoma bag. Optionally, instead of an aperture, the device can simply include markings in its central region so that an internal aperture can be cut to size and adapted for each user prior to fitting onto the stoma bag. Optionally, the internal aperture of the device can be sized and shaped to fit snugly around the aperture of the stoma bag flange. The stoma bag flange can be attached to the skin in the normal way, and the device of the invention will extend beyond the outer circumference of the stoma bag flange such that any leakage of waste material which occurs is contained by the device, thereby reducing unwanted soiling of clothes or bedding.

Advantageously, the flange extension member can include a backing layer which assists in retaining leaked waste material. The backing layer can, for example, be a sheet of waterproof or impermeable material located at the rear face of the sheet of absorbent material. For example the backing layer can be a thin film membrane, for example of polyurethane. For example the backing layer can be formed from plastics sheet. The backing layer will be located on the non-skin-facing surface of the device.

In one embodiment, the flange member of the device according to the invention is substantially circular, with the internal aperture or marking for the internal aperture being located approximately centrally. The device will therefore extend radially around the stoma so that, in whichever direction the waste material escapes, it will be contained by the device. In this embodiment, the pouch can conveniently be a segment of the circle. The chord defining the segment can be located outside the radius of the stoma bag flange. In use, the flange member is positioned so that the pouch is located with its opening uppermost, so that the contents do not fall out under gravity. However, an alternative embodiment, in which the device has an asymmetric shape is also possible and may be more desirable for some patients depending upon the configuration and topography of their stoma (and its surrounding area) which may lead to a specific location where a leak is much more likely to occur. To accommodate this, the device can have an asymmetric shape, for example the device may have "tear-drop" shape, so that a larger area of the flange extension member is placed at the location most at risk of leakage of waste material. The segment occupied by the pouch will likewise be defined by a chord across the flange extension member, located outside the radius of the stoma bag flange. Again, in use, the flange member will be positioned so that the pouch is located with its opening uppermost, so that the contents do not fall out under gravity.

The pouch in the device of the present invention can be formed by attaching a piece of planar material along a portion of the circumference (or outer edge) of the flange extension member, with the upper edge of the pouch left unattached in order to allow access to the contents of the pouch. Any form of attachment can be used, for example sewing or attachment using adhesive etc. The flange extension member forms one face of the interior of the pouch, and a second face of the interior of the pouch is provided by the piece of planar material which has been attached. Optionally the piece of planar material includes a waterproof or impermeable face and is orientated for attachment so that the second face of the interior surface of pouch is formed by the waterproof or impermeable layer. Thus, the whole of the interior of the pouch can be formed from waterproof/impermeable material. This helps to protect the contents from any leakage.

In one embodiment, the device can include adhesive located at or close to its outer edge, preferably around the outer circumference of the device. The adhesive is preferably a skin-friendly adhesive. The adhesive can be a pressure sensitive adhesive. The adhesive can be in the form of a continuous strip or can be in the form of a discontinuous strip. Preferably the adhesive is located on substantially the whole of the outer edge of the device, preferably around the whole of the outer edge of the device. Preferably the adhesive is located on substantially the whole of the outer edge of the flange extension member, preferably along the whole of the outer edge of the flange extension member. The adhesive could be located on the absorbent layer of the flange extension member or could be located on the backing layer (which could, for example be a thin film membrane). In use, this adhesive can be pressed onto the skin of the user to form a seal between the skin of the user and the outer edge of the device, which will further assist in avoiding leakage of waste material onto the user's clothing or bedding. Prior to use the adhesive on the device can be covered with a backing material. The backing material is then simply peeled off just before being brought into contact with the skin of the user during application of the device. As an alternative, adhesive can be supplied separately to the device (for example in the form of a kit with the device) and adhesive can be applied by the user so that a seal can be formed between their skin and a portion of the device at or close to its outer edge. Depending on the adhesive and the user's preference, the adhesive can be applied onto the skin, with the outer edge of the device being pressed onto the adhesive to form a seal or alternatively the adhesive can be applied onto the device just before use around (or close to) its outer edge, which is then pressed onto the skin in order to form a seal.

As noted above, the device can comprise a flange extension member having an absorbent layer. The absorbent layer used in the device according to the invention, can be provided by any suitable absorbent material or mixture of materials able to absorb liquids or semi-liquid matter. Particular mention can be made of hydrogel materials which are highly absorbent, but other suitable absorbent materials as known in the art can be used. In particular, absorbent materials suitable for other absorbent products (e.g. wounding dressing sheets, sanitary towels, infant nappies (diapers) etc.) can be used in manufacture of the device according to the present invention. It can be desirable for the absorbent material to be in sheet form, i.e. to be substantially planar. Preferably the absorbent material is selected so that the thickness of the absorbent layer is kept as low as possible in order to minimise the bulk of the combined stoma bag and device. Optionally, the absorbent layer is configured to draw any liquid or semi-liquid waste material outwardly from the stoma in order to increase the area over which the waste material is absorbed, thereby increasing its absorptive capacity and minimising contact of the waste material on the skin. The absorbent layer of the flange extension member can absorb any liquid from the waste material. Generally, where present, the absorbent layer will form the face of the flange extension member which faces the ostomate's skin which has the benefit that it provides a soft and/or non-irritant surface which is comfortable against the skin. Additionally the absorbent face can absorb any sweat produced, which will reduce chafing.

As mentioned above, the flange extension member of the device of the present invention extends beyond the outer diameter of the stoma bag flange so that leaking waste material being excreted under the flange adhesive is contained by the device. Generally, the flange extension member of the device of the present invention will extend for a predetermined distance of at least 2 cm, for example 2.5 cm, for example 3 cm or more, for example 4 cm or more, for example 5 cm or more from the outer edge of the stoma bag flange. In other words, the effective area of the device (i.e. the area able to contain the waste material) will extend for a predetermined distance of at least 2 cm, for example 2.5 cm, for example 3 cm, for example 4 cm, for example 5 cm or more beyond the stoma bag flange. Preferably the effective area of the device will extend for the predetermined distance around the whole circumference of the flange. In some embodiments a larger device may be desirable, for example either due to the degree of leakage normally experienced or for use during a specific time where leakage might be either more expected e.g. during night time or during a period where access to toilet facilities may be restricted or more difficult, for example during a concert or other activity or during travel, or simply when the ostomate has particular concerns about difficulties of accessing toilet facilities in timely manner. Accordingly in a larger device, the flange extension member can extend circumferentially beyond the stoma bag flange for at least 5 cm, for example at least 6 cm, for example at least 8 cm or even 10 cm or more, as required. The size of device required for a specific user may also vary depending on whether the ostomate has had a colostomy, ileostomy or urostomy since the physical nature of the waste (liquid v solid) will vary dependent upon the surgery performed.

The device of the present invention can be provided as a separate addition to a stoma bag, thereby allowing flexibility of choice of bag design, and also flexibility of choice of size of the device and choice regarding the size of the pouch. Additionally, use of a device which is separate to the stoma bag would be compatible with the use of drainable stoma bags, which are kept in place for longer periods and simply emptied, when required. If leakage of waste material occurs, in some circumstances only the device need be replaced, leaving the stoma bag flange and/or stoma bag in position.

In a second aspect, the present invention provides a stoma bag flange, said flange having an inner area for adhesion to the skin adjacent a stoma, and wherein a flange extension member (for example comprising a sheet of absorbent material) circumferentially surrounds the flange inner area. In this aspect, the flange extension member can be formed integrally with the stoma bag flange. The stoma bag flange of the present invention can be of particular use in "two part" stoma bags and thus, optionally, the stoma bag flange of the present invention can also include a fitting for sealing attachment with a stoma bag portion, for example by releasable connection to a mating fitting on the stoma bag portion. Such fittings are known in the art.

Alternatively the device can be formed integrally with a stoma bag. Thus, in a third aspect, the present invention further provides a stoma bag having an aperture for location around a stoma, and wherein a flange extension member (for example comprising a sheet of absorbent material and/or a thin film material) circumferentially surrounds the stoma bag aperture, and wherein said flange extension member includes a pouch for holding a spare stoma bag. The stoma bag of this aspect of the present invention can be the bag portion of a two part stoma bag system, with the bag including a fitting for sealing attachment with a stoma bag flange, for example by releasable connection to a mating fitting on the stoma bag flange. Alternatively, the stoma bag of this aspect can be a complete (one-piece) stoma bag, which comprises the flange extension member formed integrally with the bag and an integral stoma bag flange for attachment around the stoma.

In relation to the second and third aspects of the present invention, the flange extension member is preferably flexible to adapt to the contours of the user's body and can conveniently be formed from sheet material, for example from planar material. The flange extension member can comprise an absorbent layer with an absorbent face which, in use, will face the skin of the user and wherein said flange extension member extends beyond the area of the stoma bag flange which provides adhesion to the skin of the user.

Advantageously, in relation to the second and third aspects of the present invention, the flange extension member can comprise an absorbent layer with an absorbent face which assists in containing liquid content of leaked waste material. More preferably the flange extension member is a laminate comprising a layer of absorbent material and a backing layer. The backing layer can be a waterproof or impermeable layer. The backing layer can be formed from a thin film material (for example a polymeric material such as polyurethane) or can be a sheet of other waterproof or impermeable material, such as a plastics material. The backing layer can, for example, be a sheet of waterproof or impermeable material located at the rear face of the absorbent layer. The backing layer will therefore be located on the non-skin-facing surface of the device. Optionally, the waterproof or impermeable layer can be provided by an extension of the stoma bag flange.

In relation to the second and third aspects of the present invention, in one embodiment the flange extension member is substantially circular, with the internal aperture or marking for the internal aperture being located substantially centrally. The flange extension member will extend radially around the stoma such that, in whichever direction the waste material escapes, it will be contained by the flange extension member. However, an alternative embodiment, in which the flange extension member has an asymmetric shape is also possible and may be more desirable for some patients depending upon the configuration and topography of their stoma (and its surrounding area) which may lead to a specific location where a leak is much more likely to occur. To accommodate this, the flange extension member can have an asymmetric shape, for example may have "tear-drop" shape, so that a larger area of the flange extension member is placed at the location most at risk of leakage of waste material.

In one embodiment of the second and third aspects of the present invention, the flange extension member can include adhesive located at or close to its outer edge, preferably around its outer circumference. The adhesive is preferably a skin-friendly adhesive. The adhesive can be a pressure sensitive adhesive. The adhesive can be in the form of a continuous strip or can be in the form of a discontinuous strip. Preferably the adhesive is located on substantially the whole of the outer edge of the flange extension member, preferably around the whole of the outer edge of the flange extension member. The adhesive can be located on the absorbent layer of the flange extension member or could be located on the backing layer (which could, for example, be a thin film membrane). In use, this adhesive can be pressed onto the skin of the user to form a seal between the skin of the user and the outer edge of the flange extension member, which will further assist in avoiding leakage of waste material onto the user's clothing or bedding. Prior to use the adhesive can be covered with a backing material. The backing material is then simply peeled off just before the adhesive is brought into contact with the skin of the user. As an alternative, adhesive can be supplied separately to the flange or stoma bag (for example in the form of a kit with the flange or stoma bag) and adhesive can be applied by the user so that a seal can be formed between their skin and the flange extension member at or close to its outer edge. Depending on the adhesive and the user's preference, the adhesive can be applied onto the skin, with the outer edge of the flange extension member being pressed onto the adhesive to form a seal or alternatively the adhesive can be applied onto the flange extension member just before use around (or close to) its outer edge, which is then pressed onto the skin in order to form a seal.

In relation to the second and third aspects of the present invention, the flange extension member used can comprise an absorbent layer. Absorbency can be provided by any suitable absorbent material or mixture of materials able to absorb liquids or semi-liquid matter. Particular mention can be made of hydrogel materials which are highly absorbent, but other suitable absorbent materials as known in the art can be used. In particular, absorbent materials suitable for other absorbent products (e.g. wounding dressing sheets, sanitary towels, infant nappies (diapers) etc.) can be used in manufacture of the flange and/or stoma bag according to the present invention. It can be desirable for the absorbent material to be in sheet form, i.e. to be substantially planar. Preferably the absorbent material is selected so that its thickness is kept as low as possible. Optionally, in relation to the second and third aspects of the present invention, the absorbent layer of the flange extension member is configured to draw any liquid or semi-liquid waste material outwardly from the stoma in order to increase the area over which the waste material is absorbed, thereby increasing its absorptive capacity and minimising contact of the waste material on the skin. The absorbent layer of the flange extension member can absorb any liquid from the waste material. Generally, where present, the absorbent layer will form the face of the flange extension member which faces the ostomate's skin which has the benefit that it provides a soft and/or non-irritant surface which is comfortable against the skin. Additionally the absorbent face can absorb any sweat produced, which will reduce chafing.

In relation to the second and third aspects of the present invention, the flange extension member extends beyond the outer diameter of the stoma bag flange so that leaking waste material being excreted under the flange adhesive is contained by the device. Generally, the flange extension member will extend for a predetermined distance of at least 2 cm, for example 2.5 cm, for example 3 cm or more, for example 4 cm or more, for example 5 cm or more from the outer edge of the stoma bag flange. In other words, the effective area of the flange extension member (i.e. the area able to contain the waste material) will extend for a predetermined distance of at least 2 cm, for example 2.5 cm, for example 3 cm, for example 4 cm, for example 5 cm or more beyond the stoma bag flange. Preferably the effective area of the flange extension member will extend for a predetermined distance around the whole circumference of the flange. In some embodiments a larger effective area may be desirable, for example either due to the degree of leakage normally experienced or for use during a specific time where leakage might be either more expected e.g. during night time or during a period where access to toilet facilities may be restricted or more difficult, for example during a concert or other activity or during travel, or simply when the ostomate has particular concerns about difficulties of accessing toilet facilities in timely manner. Accordingly, the effective area for containment of waste material can extend circumferentially beyond the stoma bag flange for at least 5 cm, for example at least 6 cm, for example at least 8 cm or even 10 cm or more, as required. The size of the effective area required for a specific user may also vary depending on whether the ostomate has had a colostomy, ileostomy or urostomy since the physical nature of the waste (liquid v solid) will vary dependent upon the surgery performed.

Preferred or alternative features of each aspect or embodiment of the invention apply mutatis mutandis to each aspect or embodiment of the invention (unless the context demands otherwise).

The term "comprising" as used herein means consisting of, consisting essentially of, or including and each use of the word "comprising" or "comprises" can be independently revised by replacement with the term "includes", "consists essentially of" or "consists of".

These and other objects of the invention are provided by one or more of the embodiments described below.

The device, flange and stoma bag of the present invention are now described in further detail.

Figure 1:
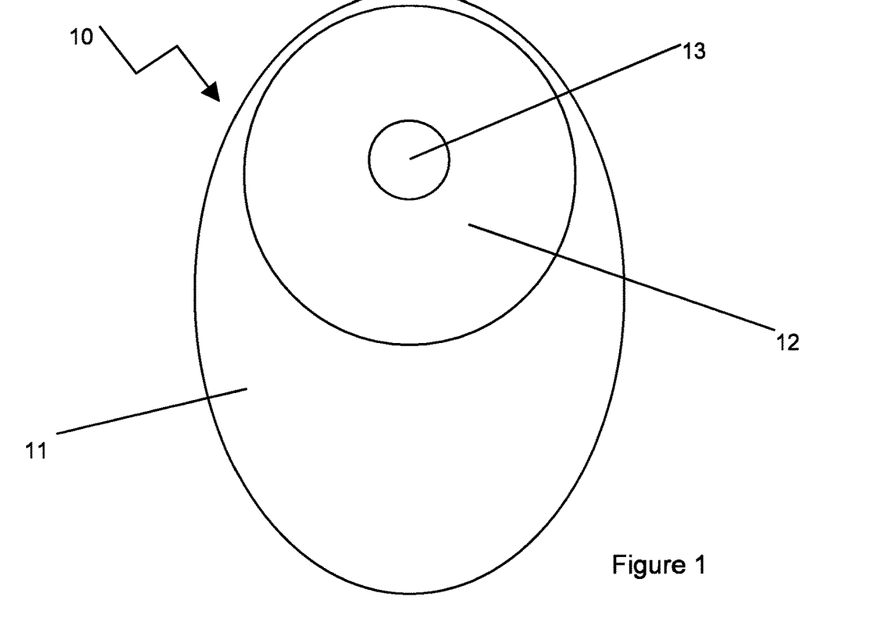
FIGS. 1 and 2 show standard stoma bags, as known in the prior art.

FIG. 1 shows a prior art stoma bag 10 which comprises a bag portion 11, usually formed of a fabric material having an inner waterproof lining and to which a thin plastic flange 12 is attached. Flange 12 defines an aperture 13 which engages with the stoma on the person's abdomen. The size of aperture 13 is selected to suit the stoma size and shape of the wearer and may be cut to size prior to use. The flange portion 12 can be coated with a band of skin-friendly adhesive (not shown) which is pressed onto to the skin of the abdomen around the stoma. The seal between the stoma bag flange 12 and the user's skin is relied upon to prevent unwanted leakage of the material egressing from the stoma. As an alternative to the flange 12 being formed integrally with bag portion 11, the flange 12 can be adapted to engage with a fitting on bag portion 11 in a sealing manner. Thus flange 12 is first attached to the skin of the abdomen by means of a skin-friendly adhesive placed over the surface of flange 12. Once flange 12 has been suitably secured, bag portion 10 is then located onto flange 12 and attached thereto. The stoma bag 10 illustrated in FIG. 1 is of a "closed" type, that is to say the bag is sealed all around its outer edge and the bag when containing waste material is simply detached and disposed of before a new bag is fitted.

Figure 2:
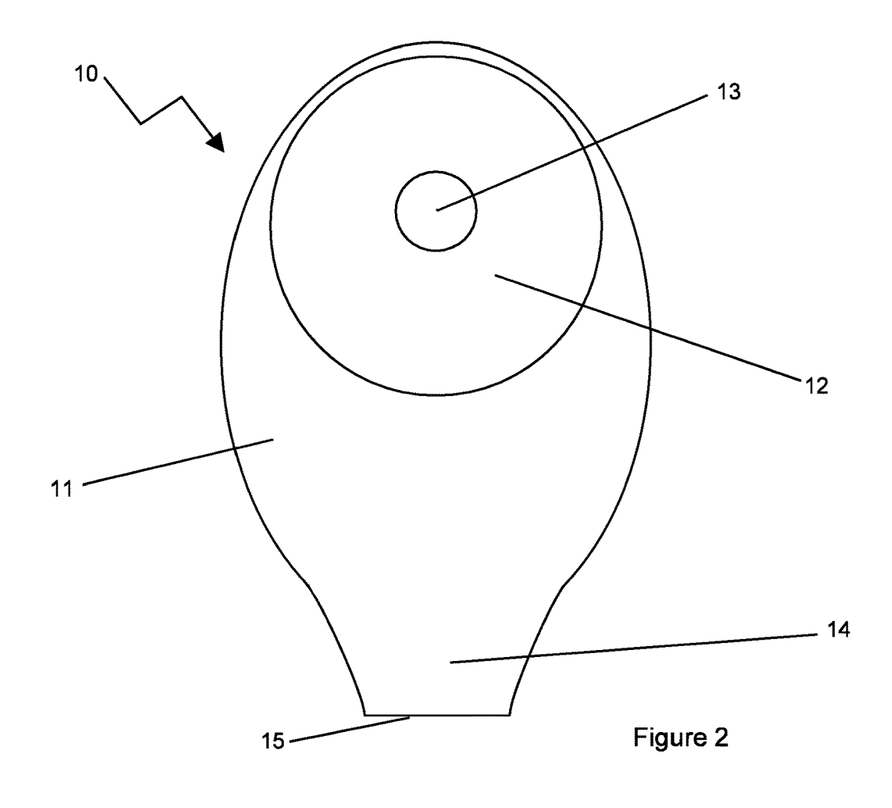

FIG. 2 illustrates an alternative form of known stoma bag 10. Again, bag 10 comprises a bag portion 11 having a flange 12 which defines aperture 13. The size of aperture 13 is selected to suit the stoma size and shape of the user and may be cut to size prior to use. As with the bag of FIG. 1, flange 12 is coated with an adhesive which is suitable for attachment to the skin of the abdomen around the stoma. The seal between the stoma bag flange and the skin is relied upon to prevent unwanted leakage of the material egressing from the stoma. As an alternative to the flange 12 being formed integrally with bag portion 11, the flange 12 can be a separate element which is first attached to the skin before engaging with a fitting on bag portion 11 in a sealing manner. In contrast to the stoma bag shown in FIG. 1, the bag of FIG. 2 is drainable and has an outlet 15 at its lower edge 14. Outlet 15 allows the contents of bag 10 to be evacuated, thereby allowing bag 10 to be worn for a longer period before replacement. The bag 10 illustrated in FIG. 2 is more suitable for an ileostomy or a urostomy, where the material evacuating from the stoma is of a generally fluid character, whereas the bag illustrated in FIG. 1 would more commonly be used for a colostomy.

Figure 3:
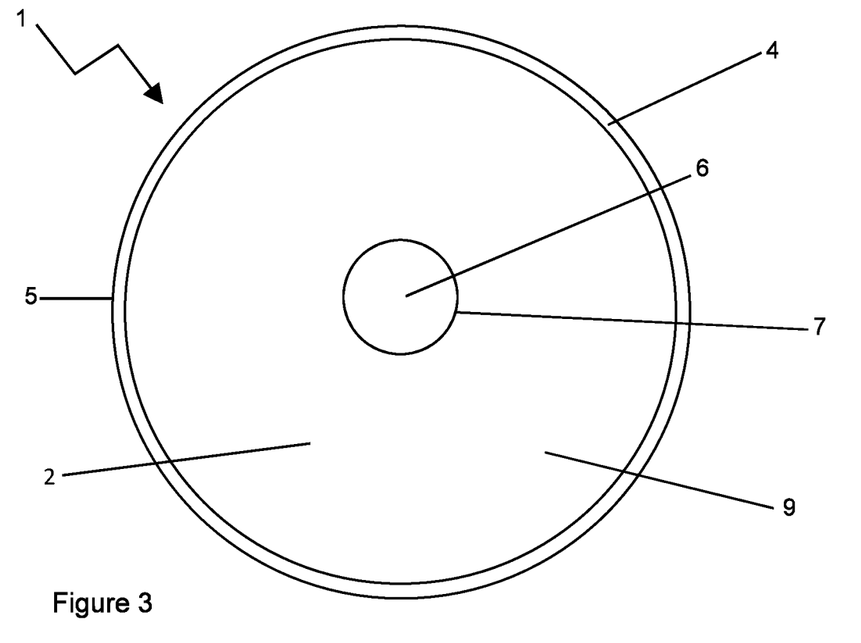
FIG. 3 shows the front view of one embodiment of a device according to the present invention.

FIG. 3 shows the front of one embodiment of a device 1 according to the first aspect of the present invention. As illustrated, device 1 comprises a flange extension member 9 formed from substantially planar sheet material, which comprises an absorbent layer 2. In use, absorbent layer 2 is placed towards the skin of the user. In the embodiment shown in FIG. 3, device 1 has a flange extension member 9 which is of a generally circular configuration, but other shapes are also possible, including elliptical or asymmetric shapes, depending upon the requirements and/or preferences of the user. As shown device 1 includes an aperture 6 which is generally centrally located within the device 1. Aperture 6 may be reinforced around its circumference 7 with an additional reinforcing means (not shown). Aperture 6 is sized and shaped to cooperate with the flanged portion 12 of stoma bag 10. To locate device 1 onto stoma bag 10, the bag portion 11 (which is of a flexible material) can be fed through aperture 6 so that the device 1 is positioned between flange 12 and bag portion 11 of stoma bag 10. The outer periphery 5 of device 1 can also be reinforced with an additional reinforcing means (not shown) or could be bonded (for example by adhesive, sewing or by heat bonding) to provide a neat edge. Preferably, adhesive material 4 (optionally covered by a backing material prior to use) can be located around the outer edge of device 1 on the flange extension member 9 at or close to its outer edge. As illustrated adhesive material 4 is located at the outer periphery 5 of the flange extension member 9, but could alternatively be positioned slightly inside periphery 5. Adhesive material 4 is shown in the form of a continuous strip present over the whole of the outer circumference of sheet 9, but a discontinuous band of adhesive or a partial band of adhesive could be sufficient for some users. Adhesive material 4 can be any adhesive material (including a pressure sensitive adhesive) which is compatible with application to skin and such adhesives are well known in the art and indeed would normally be applied to the skin facing face of flange 12. Adhesive material 4 can be used to provide a seal between flange extension member 9 of device 1 and the skin of the user to assist in containing any waste material which has leaked out from the junction between stoma bag 10 and the stoma. In an alternative embodiment, the strip of adhesive material 4 need not be present but adhesive could be applied separately so that a seal between the outer edge portion of flange extension member 9 is formed with the skin of the user.

Flange extension member 9 can be substantially formed from a sheet of absorbent material 2, having an absorbent face which is placed toward the user. Flange extension member can comprise activated carbon or charcoal which acts to absorb any unpleasant odour in the event of a leakage. More preferably, however, sheet material 9 is a laminate comprising a layer of absorbent material 2 and a waterproof or impermeable backing layer 3. Backing layer 3 can be a thin film material (such as a thin film membrane, for example a polyurethane membrane) or could be a sheet of plastics material.

Figure 4:
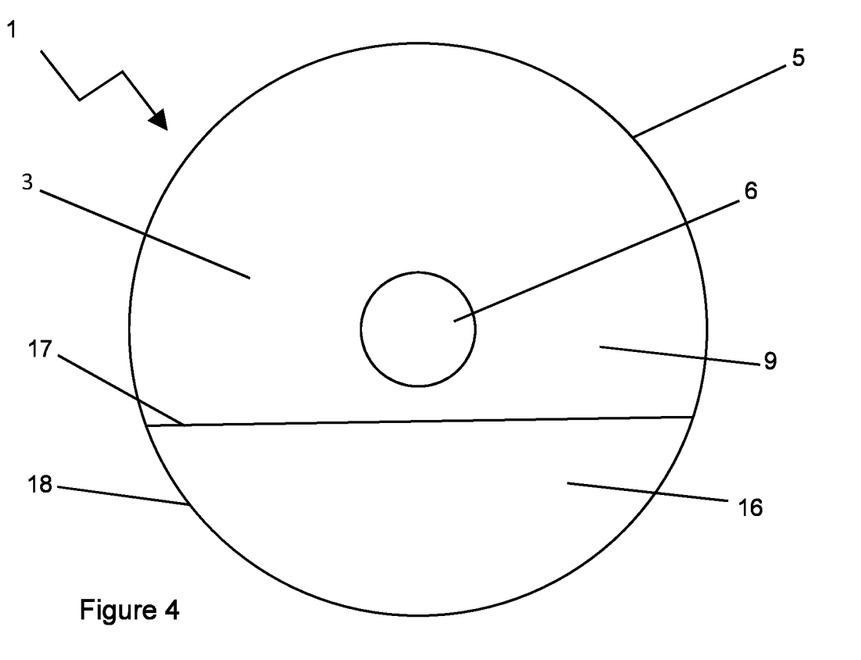
FIG. 4 shows the rear view of the embodiment as shown in FIG. 3 and illustrates the pouch.

FIG. 4 shows the reverse side of device 1 illustrated in FIG. 3. Flange extension member 9 of device 1 can conveniently comprise a waterproof or impermeable layer 3, which assists in retaining any waste material being contained by device 1, for example by absorption by the absorbent layer 2. In use the waterproof or impermeable layer 3 of device 1 would be positioned outwardly, i.e. to be in contact with the clothes of the user. FIG. 4 illustrates the pouch of the present invention which is matched to the outer periphery of flange 9 and occupies a segment of the shape of flange 9. In use, device 1 is worn so that the edge 17 of pouch 16 is uppermost, so that the contents of pouch 16 are held securely. Pouch 16 can be formed by attaching a piece of planar material along the curved side 18, leaving upper edge 17 free to allow access to the contents of pouch 16. The waterproof or impermeable layer 3 forms one face of the interior surface of pouch 16. The second face of the interior surface of pouch 16 is provided by the additional planar material. Optionally the second face of the interior surface of pouch 16 can include a waterproof or impermeable layer. Thus, the whole of the interior of pouch 16 is formed from waterproof/impermeable material. This helps to protect the contents from any leakage.

Figure 5:
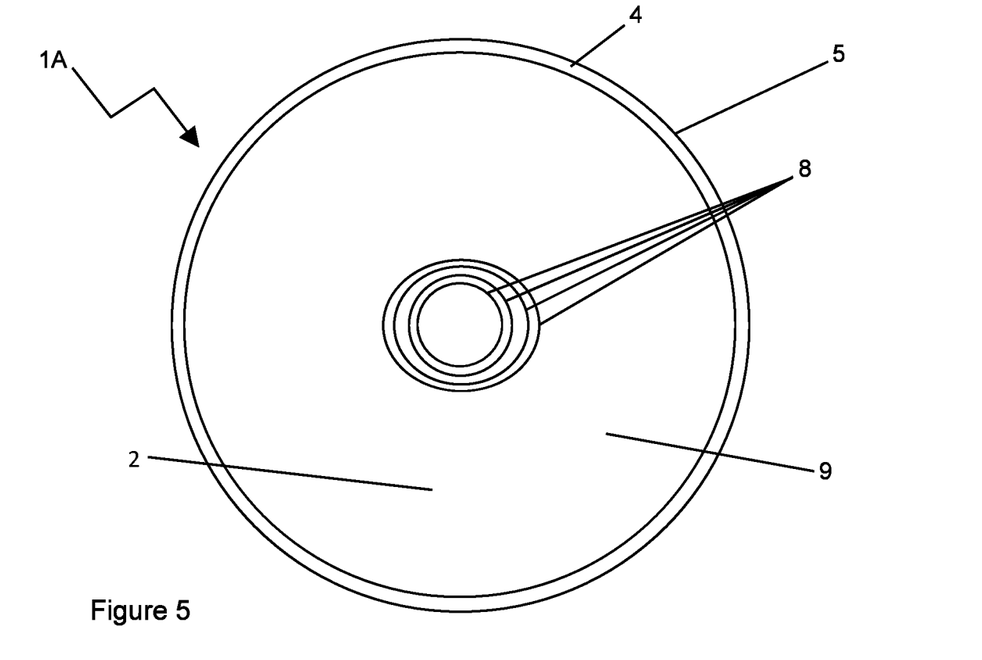
FIG. 5 shows the front view of an alternative embodiment of a device according to the present invention.
Figure 6:
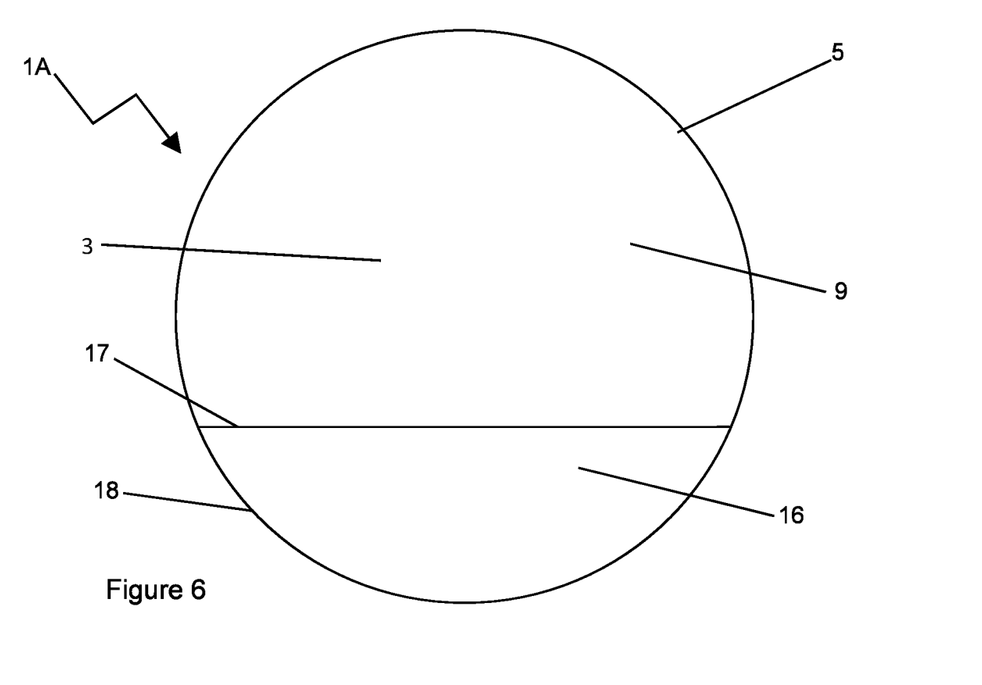
FIG. 6 shows the rear view of the embodiment as shown in FIG. 5 and illustrates the pouch.

FIG. 5 shows the front face of a different embodiment of a device 1A according to the present invention. Device 1A comprises flange extension member 9 formed from a substantially planar sheet material, which comprises an absorbent layer 2. Absorbent layer 2 is placed towards the skin of the user when in use. Device 1A as illustrated has a flange extension member 9 which is of a generally circular configuration, although other shapes are also possible depending on the requirements and/or preferences of the user. For example elliptical or asymmetric shapes could alternatively be used. FIG. 6 shows the reverse face of the device 1A shown in FIG. 5. FIG. 6 illustrates the pouch of the present invention which is matched to the outer periphery of flange 9 and occupies a segment of the shape of flange 9. In use, device 1A is worn so that the edge 17 of pouch 16 is uppermost, so that the contents of pouch 16 are held securely. Pouch 16 can be formed by attaching a piece of planar material along the curved side 18 of member 9, leaving upper edge 17 free to allow access to the contents of pouch 16. The waterproof or impermeable layer 3 forms one face of the interior surface of pouch 16. The second face of the interior surface of pouch 16 is provided by the additional planar material. Optionally the second face of the interior surface of pouch 16 can include a waterproof or impermeable layer. Thus, the whole of the interior of pouch 16 is formed from waterproof/impermeable material. This helps to protect the contents from any leakage.

As can be seen, device 1A does not include an aperture, but does have markings or indices 8 located on the face of absorbent layer 2. Alternatively or additionally, markings or indices 8 could be shown on the reverse face 3. Thus the appropriate aperture size and shape suitable for cooperation with a user's stoma could be selected and the appropriate marking for the boundary of that aperture used as a guide in creating the aperture, for example by cutting through device 1A with scissors or other suitable cutting means. Use of such markings or indices 8 provides increased flexibility of the device 1A, making it suitable for use with different stoma sizes, and by allowing a greater variation in size and shape of aperture. To locate device 1A onto stoma bag 10 prior to use of bag 10, the bag portion 11 can be simply fed through the aperture created in device 1A until device 1A is located between stoma bag flange 12 and bag portion 11 of stoma bag 10.

As illustrated, the outer periphery 5 of device 1A could be reinforced with an additional reinforcing means (not shown) or could be bonded (for example by adhesive, sewing or by heat bonding) to provide a neat edge. Advantageously, adhesive material 4 can be located substantially around the outer periphery of device 1A on flange extension member 9. As illustrated, adhesive material 4 is located at the outer periphery 5 device 1A, but adhesive material 4 could alternatively be positioned slightly inside periphery 5. Adhesive material 4 would normally be protected by a backing material (not shown) prior to use. FIG. 5 shows adhesive material 4 as a continuous strip located all around the edge of flange extension member 9, but a discontinuous band of adhesive or a partial band of adhesive could be sufficient for some users. The adhesive used in the strip of adhesive material 4 could be any suitable adhesive material (including a pressure sensitive adhesive) which is compatible with adhering a medical device and which provides a secure fit to the skin of the user. In use adhesive material 4 provides a seal between device 1A and the abdomen of the user. Such a seal helps to assist in retaining any waste material which has leaked out from the junction between stoma bag 10 and the user's stoma and thereby contains the waste material within the device. For example, liquid or semi-liquid waste material can be absorbed by absorbent layer 2. In an alternative embodiment, the strip of adhesive material 4 need not be present but adhesive could be applied separately so that a seal between the outer edge portion of device 1A is formed with the skin of the user.

Figure 7:
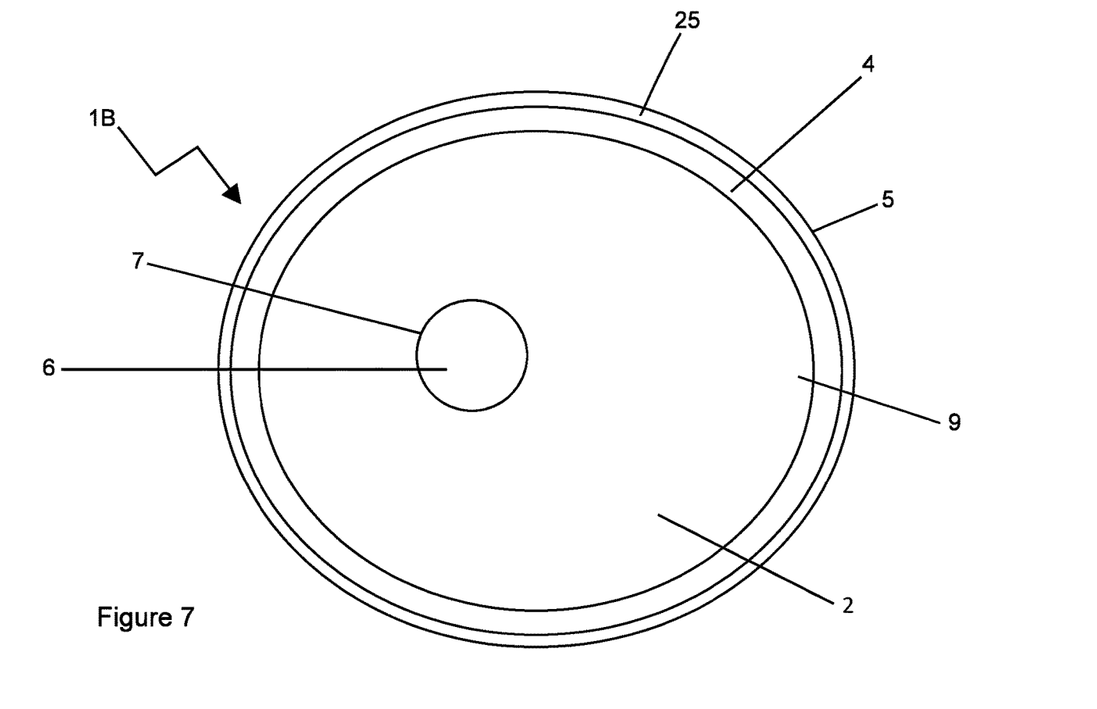
FIG. 7 shows the front view of a further embodiment of the device according to the present invention.
Figure 8:
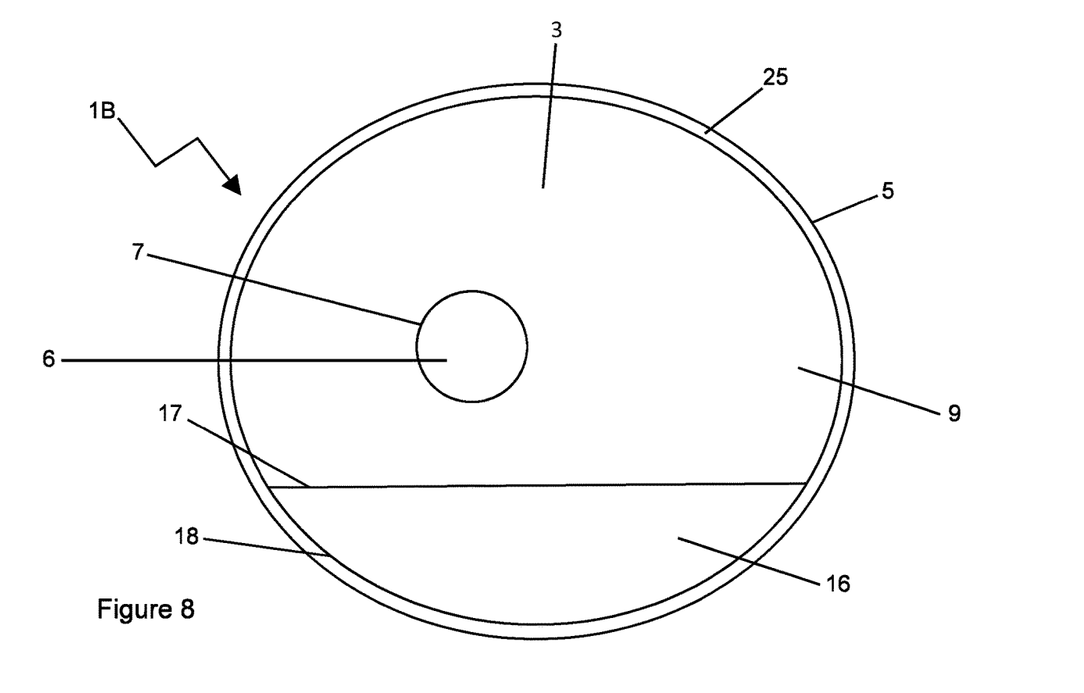
FIG. 8 shows the rear view of the embodiment as shown in FIG. 7 and illustrates the pouch.

FIG. 7 shows the front face of a further embodiment of a device 1B also according to the present invention. As illustrated, device 1B comprises flange extension member 9 formed from a substantially planar material having an absorbent layer 2. The outer face of absorbent layer 2 would be placed towards the skin of the user in use. The reverse face of device 1B is shown in FIG. 8 and includes an impermeable or waterproof layer 3 which acts as a backing layer to prevent seepage of waste material through device 1B. Backing layer 3 can be a thin film material (such as a thin film membrane, for example a polyurethane membrane) or could be a sheet of plastics material.

FIG. 7 illustrates the use of reinforcing material 25 at the periphery 5 of device 1B.

Reinforcing material 25 bonds the absorbent layer 2 and backing layer 3 together into a laminate structure. As an alternative to using reinforcing material 25, the layers forming flange extension member 9 can be secured together at the outer edge 5 by different means, for example the layers can be heat bonded or secured by sewing or adhered by other means, for example by adhesive. Adhesive material 4 is located adjacent to reinforcing material 25, and around the circumference of flange extension member 9, close to its outer edge. In an alternative embodiment, the adhesive could be located on the reinforcing material 25 or adhesive could be applied separately so that a seal between the outer edge portion of device 1B is formed with the skin of the user. Adhesive material 4 is shown as being present as a continuous strip located all around the edge of flange extension member 9, but a discontinuous band of adhesive or a partial band of adhesive could be sufficient for some users. Similarly to the device 1 shown in FIGS. 3 and 4, the device 1B includes a pre-cut aperture 6. Alternatively, aperture 6 of device 1B could be replaced by markings or indices 8 as in device 1A of FIGS. 5 and 6. An aperture of appropriate size for a user's stoma and at the required location would then be cut in device 1B prior to use, for example using scissors. The periphery 7 of aperture 6 can include a strip of reinforcing material (equivalent to reinforcing material 25) which bonds the layers making up flange extension member 9 together at the internal aperture or alternatively the layers forming flange extension member 9 can be secured at periphery 7 by other means, for example by heat bonding, sewing or adhesion. Device 1B differs to the other embodiments illustrated in FIGS. 2 to 6 since flange extension member 9 has an asymmetric or elliptical shape, with the aperture 6 being located off-set from the centre of device 1B. This configuration allows a greater area effective for containing waste material to be located at a specific position where there is a higher likelihood of leakage occurring. An increased likelihood of leakage at one particular location can occur due to the precise shape of a stoma (which may not be perfectly symmetrical) or due to an asymmetric topology in the abdomen of the user, for example due to scarring, puckering in the skin or the like. Device 1B therefore has particular relevance and may be especially advantageous for users experiencing an increased likelihood of leakage of waste material at one particular location around their stoma.

FIG. 8 illustrates the pouch of the present invention which is matched to the outer periphery of flange 9 and occupies a segment of the shape of flange 9. In use, device 1B is worn so that the edge 17 of pouch 16 is uppermost, in order that the contents of pouch 16 are held securely. Pouch 16 can be formed by attaching a piece of planar material along the curved side 18, leaving upper edge 17 free to allow access to the contents of pouch 16. The waterproof or impermeable layer 3 forms one face of the interior surface of pouch 16. The second face of the interior surface of pouch 16 is provided by the additional planar material. Optionally the second face of the interior surface of pouch 16 can include a waterproof or impermeable layer. Thus, the whole of the interior of pouch 16 is formed from waterproof/impermeable material. This helps to protect the contents from any leakage.

Figure 9:
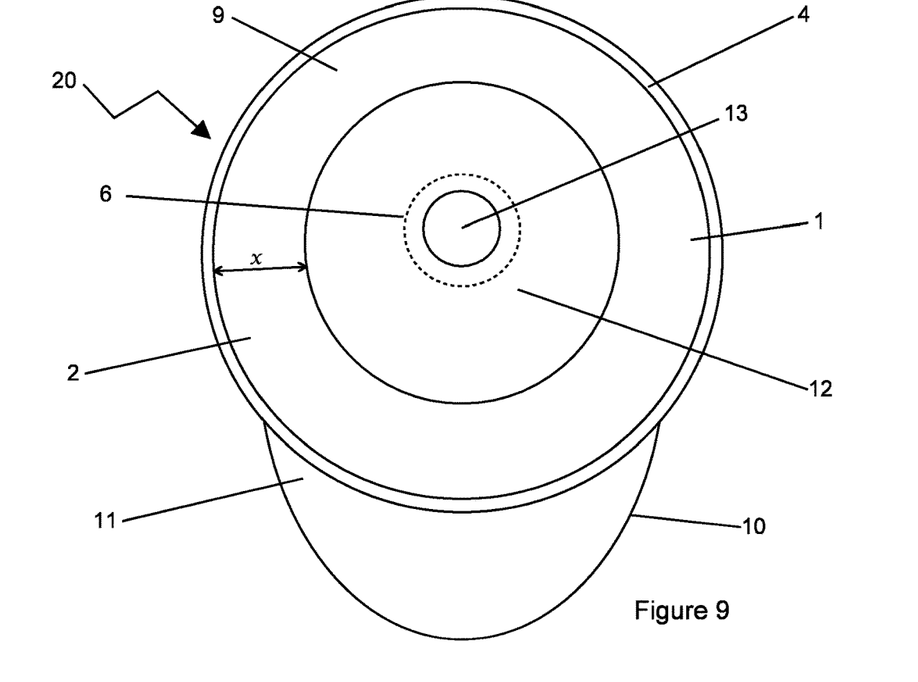
FIG. 9 shows front view of the device of FIG. 3 positioned on the stoma bag of FIG. 1.
Figure 10:
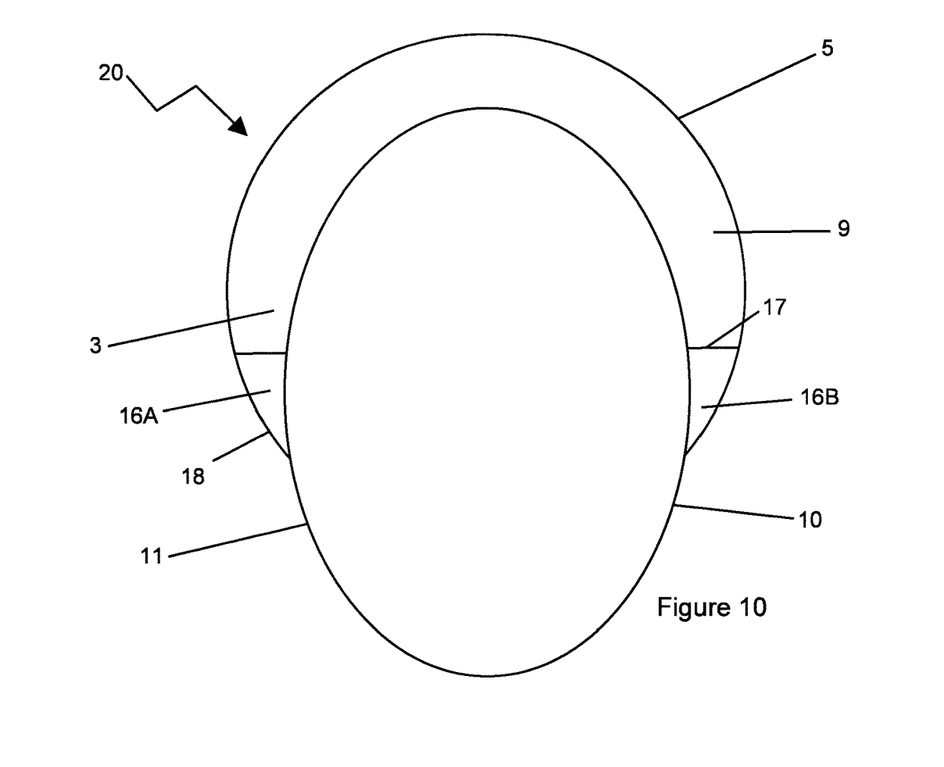
FIG. 10 shows the rear side of the device of FIG. 3 positioned on the stoma bag of FIG. 1 with the pouch partially visible.

FIG. 9 shows the front face of an improved stoma bag 20, either formed using the device 1 of FIG. 3 on a conventional prior art stoma bag 10 or alternatively formed using the device 1A of FIG. 5 on a conventional stoma bag 10, following the creation of an aperture suitable for the user's stoma within device 1A (simply for convenience, the device is referenced by reference numeral "1" in FIGS. 9 and 10). The rear face of the improved stoma bag is shown in FIG. 10. Stoma bag 10 as illustrated is a closed bag (for example as shown in FIG. 1), but an open (or drainable) bag (for example as shown in FIG. 2) could alternatively be used. The flange extension member 9 of device 1 is located between flange 12 and bag portion 11 of stoma bag 10, and is partially covered by flange 12 of stoma bag 10. Flange extension member 9 comprises a layer of absorbent material 2 and a backing layer 3. Backing layer 3 can be a thin film material (such as a thin film membrane, for example a polyurethane membrane) or could be a sheet of plastics material.

Device 1 extends beyond flange 12 and therefore provides an effective area of flange extension member 9 for containment of waste material. The effective area of flange extension member 9 is bounded by the outer edge of flange extension member 9 and the outer edge of stoma bag flange 12. Any waste material leaking out beyond flange 12 can be contained within this effective area, for example can be absorbed by this the absorbent material of layer 2 if the waste material is liquid or semi-liquid or can be simply contained by device 1 where the waste material is more solid. In use, the front face of the stoma bag 20 as illustrated in FIG. 9 would be placed towards the skin of the user so that aperture 13 is located around the stoma of the user and the absorbent layer 2 contacts the skin. Aperture 13 is of course aligned with aperture 6 of device 1 (shown in dotted outline, for illustration only). A biocompatible adhesive is used to attach flange 12 onto the abdominal skin of the user, and is pressed firmly onto the skin to ensure that the adhesive is securely bonded. The adhesive can be a pressure sensitive adhesive. The adhesive may be pre-coated onto the front face of flange 12 (and optionally covered by a backing sheet prior to use) or alternatively a suitable amount of adhesive can be applied onto the flange or skin and used to secure flange 12 and skin together. Flange 12 can be formed integrally with bag portion 11 or can be formed independently. Where the flange 12 is non-integral with bag portion 11, it is necessary for bag portion 11 to be attached or otherwise sealingly secured onto flange 12 to form a complete stoma bag 10. Once flange 12 has been securely adhered to the skin of the user, the adhesive material 4 located around the outer edge of the flange extension member 9 is then pressed into place and again secured to the abdominal skin of the user. Should any waste material escape from the stoma and leak beyond the adhesive face of flange 12, this waste material will be contained by the flange extension member 9 surrounding flange 12. Liquid or semi-liquid waste material will be quickly absorbed by the absorbent layer 2 of the sheet material 9 in device 1. The flange extension member can also include activated carbon or charcoal to assist in odour control. Adhesive 4 will further assist in retaining the waste material from contacting clothes or bedding next to the user. Such leakage will therefore be prevented from soiling the user's clothes or bedding. Seepage of waste material out of device 1 is also prevented from causing soiling due to impermeable layer 3 located at the rear of the flange extension member 9 (see FIG. 10). The pouch is attached to the flange extension member 9 is the same way as shown in FIGS. 4 and 6. Portions 16A and 16B of the pouch are visible in FIG. 10 as the pouch is positioned behind stoma bag 11.

As shown in FIG. 9, the flange extension member 9 in device 1 extends beyond the outer edge of flange 12 by a distance x for form an effective area for containment of waste material. Generally distance x will be at least 2 cm, all around the circumference of flange 12. Distance x can be greater than 2 cm, e.g. can be 2.5 cm. Generally distance x will be of from 2 cm to 6 cm (e.g. 2.5 cm to 6 cm). Distance x can be substantially constant around the circumference of flange 12. Alternatively distance x can be vary around the circumference of flange 12, as the device 1 need not be symmetrical (as shown), but could have an increased area of flange extension member 9 at one or more locations, for example as illustrated in FIG. 7. The flange extension member can also include activated carbon or charcoal to assist in odour control. FIG. 10 shows the rear or outward face of the improved stoma bag 20 and illustrates the impermeable layer 3 of device 1.

Figure 11:
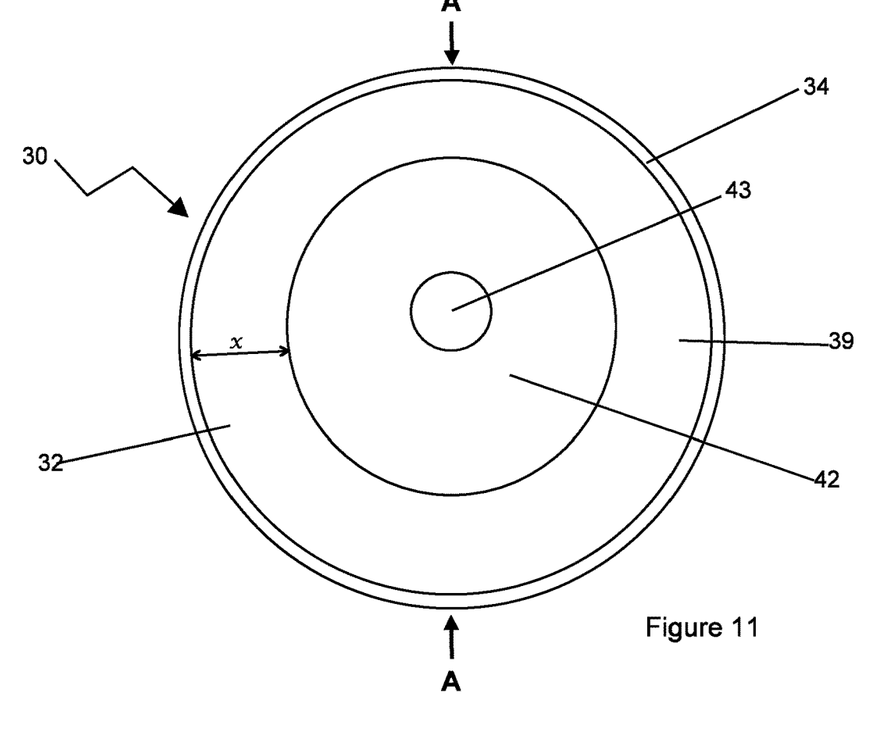
FIG. 11 shows the front view of a flange according to the second aspect of the invention.
Figure 12:
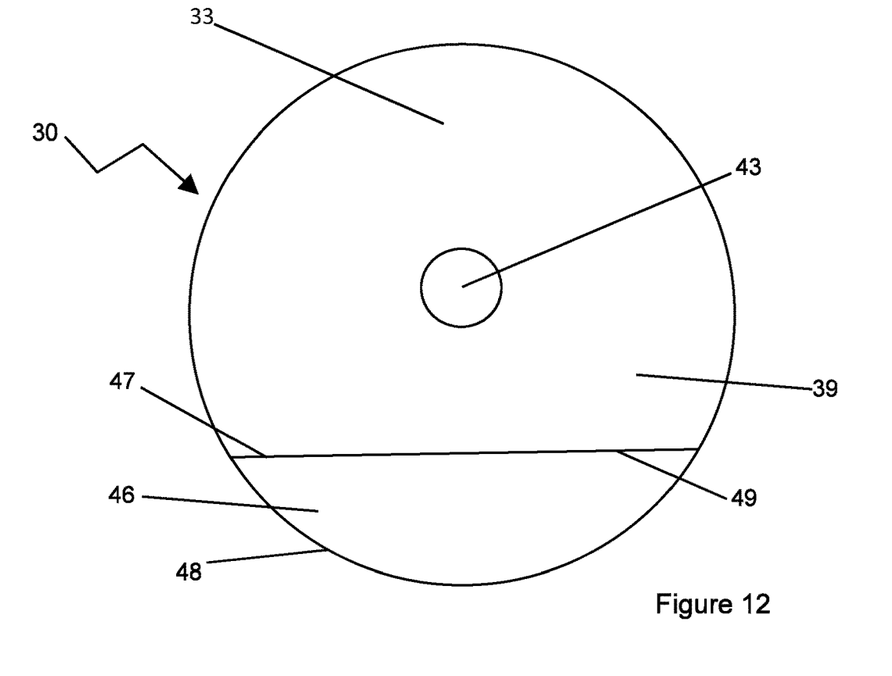
FIG. 12 shows the rear view of the flange shown in FIG. 11 and illustrates the pouch.

The present invention also provides a stoma bag flange 30, which is shown in FIGS. 11 and 12. Flange 30 could be used with a two part stoma bag or could form part of a one-piece stoma bag. Flange 30 comprises a flange inner area 42 for adhesion to the user's skin and a flange extension member 39 which comprises an absorbent layer 32. Flange extension member 39 circumferentially surrounds flange inner area 42. In use, absorbent layer 32 (which forms one face of flange extension member 39) would be placed towards the skin of the user, with aperture 43 located around the stoma of the user. A biocompatible adhesive is used to attach flange inner area 42 onto the abdominal skin of the user, and is pressed firmly onto the skin to ensure that the adhesive is securely bonded. The adhesive can be a pressure sensitive adhesive. The adhesive may be pre-coated onto the front face of the flange inner area 42 (and optionally covered by a backing sheet prior to use) or alternatively a suitable amount of adhesive can be applied onto the flange inner area 42 or the area of skin around the stoma and used to secure the flange inner area 42. Flange 30 can be formed integrally with a stoma bag portion (not shown) or can be formed independently. Where the flange 30 is non-integral with a stoma bag portion 11, it is necessary for bag portion 11 to be attached or otherwise sealingly secured onto flange inner area 42 to form a complete stoma bag 10. A mating fitting (not shown) may therefore be provided on flange inner area 42 for secure attachment to a stoma bag portion. Once flange inner area 42 has been securely adhered to the skin of the user, the adhesive material 34 located around the outer edge of flange 30 (at the edge of flange extension member 39) is then pressed into place and again secured to the abdominal skin of the user. Should any waste material escape from the stoma and leak beyond the adhesive face of flange inner area 42, this waste material will be contained by the flange extension member 39 around flange inner area 42. Liquid or semi-liquid waste material will be quickly absorbed by the absorbent layer 32 of the flange extension member 39 in flange 30. Solid waste will simply be contained by flange extension member 39. The flange extension member can also include activated carbon or charcoal to assist in odour control. Adhesive 34 will further assist in containing the waste material and preventing it from contacting clothes or bedding next to the user. Such seepage will therefore be prevented from soiling the user's clothes or bedding.

As illustrated in FIG. 11, the flange extension member 39 extends beyond the outer edge of flange inner area 42 by a distance x. Generally distance x will be at least 2 cm, all around the circumference of flange inner area 42 and this forms the effective area for containment of waste material. Distance x can be greater than 2 cm, e.g. 2.5 cm. Generally distance x will be of from 2 cm to 6 cm (e.g. 2.5 cm to 6 cm). Distance x can be substantially constant around the circumference of flange inner area 32.

Alternatively distance x can be vary around the circumference of flange inner area 42, as the flange extension member 39 need not be symmetrical (as shown), but could have an increased area of at one or more locations, for example could be of an elliptical shape similarly to the device as illustrated in FIG. 7.

FIG. 12 shows the rear or outward face of the flange 30 and illustrates the impermeable backing layer 33 located to the rear of the layer of absorbent material 32 and also forming part of the flange extension member 39. Backing layer 33 can be a thin film material (such as a thin film membrane, for example a polyurethane membrane) or could be a sheet of plastics material.

FIG. 12 again illustrates the pouch of the present invention which is matched to the outer periphery of flange 39 and occupies a segment of the shape of flange 39. In use, device 30 is worn so that the edge 47 of pouch 46 is uppermost, so that the contents of pouch 46 are held securely. Pouch 46 can be formed by attaching a piece of planar material along the curved side 48, leaving upper edge 47 free to allow access to the contents of pouch 46. The waterproof or impermeable layer 33 forms one face of the interior surface of pouch 16. The second face of the interior surface of pouch 46 is provided by the additional planar material. Optionally the second face of the interior surface of pouch 46 can include a waterproof or impermeable layer. Thus, the whole of the interior of pouch 46 is formed from waterproof/impermeable material. This helps to protect the contents from any leakage.

Figure 13:
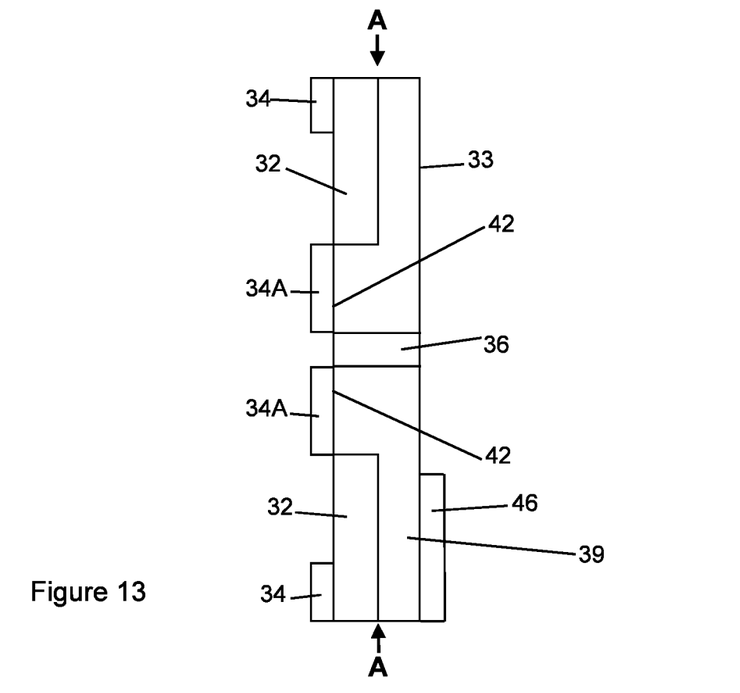
FIG. 13 is a cross-sectional view along line A-A of one embodiment of the flange shown FIG. 11.

As shown in FIG. 13 (a cross-section along line A-A of FIG. 11), in one embodiment, the impermeable backing layer 33 can be a continuation of flange inner area 42, which runs behind the absorbent layer 32. Both impermeable layer 33 and absorbent layer 32 together form flange extension member 39. As illustrated, the flange inner area 42 is shown having an increased thickness relative to the remainder of the flange 30. However, in embodiments where the materials concerned are very thin, such increased thickness in the flange inner area 42 may not be necessary. Flange inner area 42 is coated with a layer of skin-friendly adhesive 34A, which may optionally be covered by a backing sheet (not shown prior to use). Adhesive 34A could be applied to flange inner area by the user immediately before application to the skin. Alternatively adhesive 34A could be omitted from the flange, with the user applying adhesive to their skin and then bringing the flange inner area 42 into contact with such adhesive. Impermeable layer 33 and absorbent layer 32 together form flange extension member 39. The absorbent layer 32 can include particles of activated carbon or charcoal to assist with odour control. Adhesive 34 is located at or close to the outer edge of flange extension member 39 to enable the edge of flange extension member 39 to be adhered to the skin of the user during use. In use aperture 36 through flange extension member 39 is coaxially aligned with the stoma so that output from the stoma can pass through aperture 36 to a stoma bag portion (not shown) and collected therein. Pouch 46 is shown attached to flange extension member 39.

Figure 14:
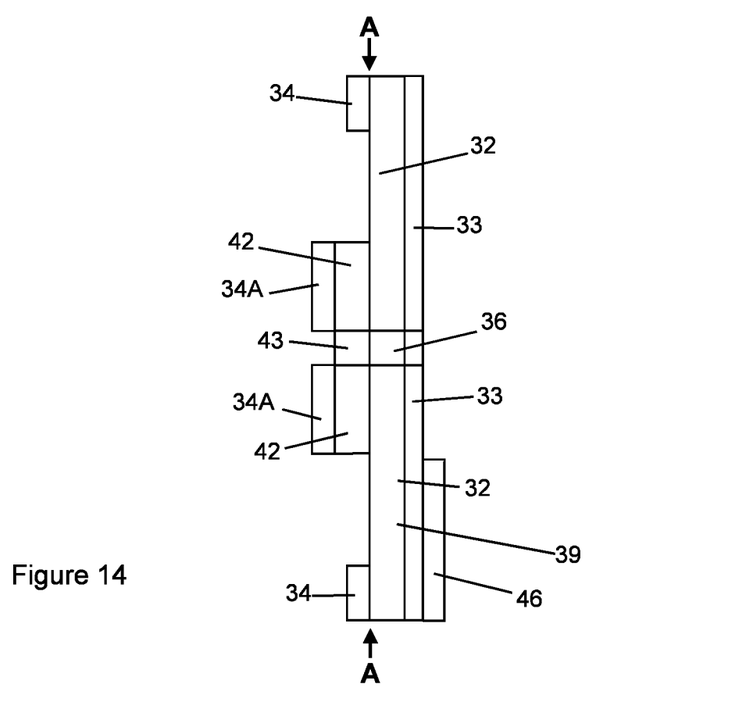
FIG. 14 is a cross-sectional view along line A-A of an alternative embodiment of the flange shown in FIG. 11.

FIG. 14 shows an alternative arrangement which could be used for the flange 30 of FIGS. 11 and 12, again in cross-section along line A-A of FIG. 11. As illustrated, the absorbent layer 32 lies behind flange inner area 42. Impermeable backing layer 33 is located behind the absorbent layer 32. Again, both impermeable backing layer 33 and absorbent layer 32 together form flange extension member 39. The absorbent layer 32 can include particles of activated carbon or charcoal to assist with odour control. Flange inner area 42 is coated with a layer of skin-friendly adhesive 34A, which may optionally be covered by a backing sheet (not shown prior to use). Adhesive 34A could be applied to flange inner area by the user immediately before application to the skin. Alternatively adhesive 34A could be omitted from the flange, with the user applying adhesive to their skin and then bringing the flange inner area 42 into contact with such adhesive. Adhesive 34 is located at or close to the outer edge of flange extension member 39 to enable the edge of flange extension member 39 to be adhered to the skin of the user during use. Aperture 43 through the flange inner area 42 is aligned with aperture 36 through flange extension member 39, and in use are also coaxially aligned with the stoma so that output from the stoma can pass through apertures 43 and 36 to a stoma bag portion (not shown) and collected therein. Pouch 46 is shown attached along edge 48 to flange extension member 39. Access to pouch 46 is via free edge 49.

Figure 15:
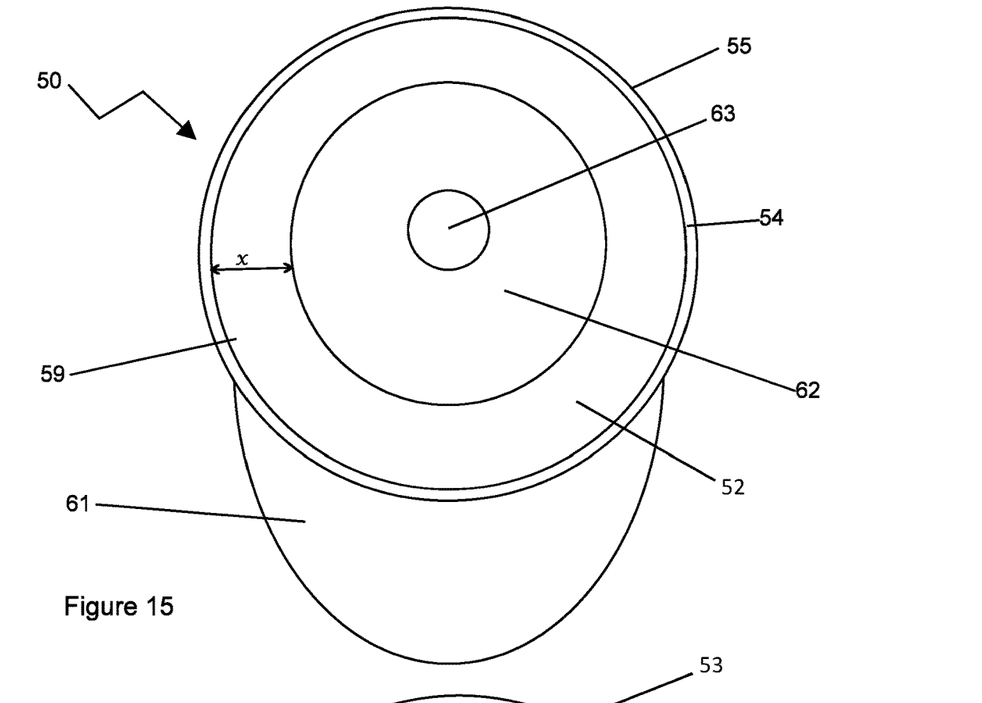
FIG. 15 shows the front view of a stoma bag according to the third aspect of the invention.

FIG. 15 shows an embodiment of a stoma bag 50 according to the third aspect of the present invention. Stoma bag 50 comprises a stoma bag flange 62 for adhesion to the user's skin and a flange extension member 59. Flange extension member 59 is substantially planar and as illustrated comprises a layer of absorbent material 52. Flange extension member 59 circumferentially surrounds flange 62. In use, absorbent layer 52 would be placed towards the skin of the user, with aperture 63 located around the stoma of the user. A biocompatible adhesive is used to attach flange 62 onto the abdominal skin of the user, and is pressed firmly onto the skin to ensure that the adhesive is secured bonded. The adhesive can be a pressure sensitive adhesive. The adhesive may be pre-coated onto the front face of the flange 62 (and optionally covered by a backing sheet prior to use) or alternatively a suitable amount of adhesive can be applied onto the flange 62 or skin and used to secure the flange 62. Stoma bag 50 is formed integrally with a stoma bag portion 61. Whilst a closed bag is illustrated in FIG. 15, the invention can also be used with a drainable bag (similar to the stoma bag of FIG. 2). Once flange 62 has been securely adhered to the skin of the user, the adhesive material 54 located around the outer edge 55 of flange extension member 59 can then be pressed into place and secured to the abdominal skin of the user. Should any waste material escape from the stoma and leak beyond the adhesive face of flange 62, this waste material will be contained by the flange extension member 59 around flange 62. Liquid or semi-liquid waste material will be quickly absorbed by the absorbent layer 52. Adhesive 54 will further assist in containing the waste material and preventing it from contacting clothes or bedding next to the user.

As illustrated, the flange extension member 59 extends beyond flange 62 by a distance x. Generally distance x will be at least 2 cm, all around the circumference of flange 62 and this forms the effective area for containment of waste material.

Distance x can be greater than 2 cm, e.g. 2.5 cm. Generally distance x will be of from 2 cm to 6 cm (e.g. 2.5 cm to 6 cm). Distance x can be substantially constant around the circumference of flange 62. Alternatively distance x can be vary around the circumference of flange 62, as the flange extension member 59 need not be symmetrical (as shown), but could have an increased area of at one or more locations, for example could be of an elliptical shape similarly to the device as illustrated in FIG. 7.

Figure 16:
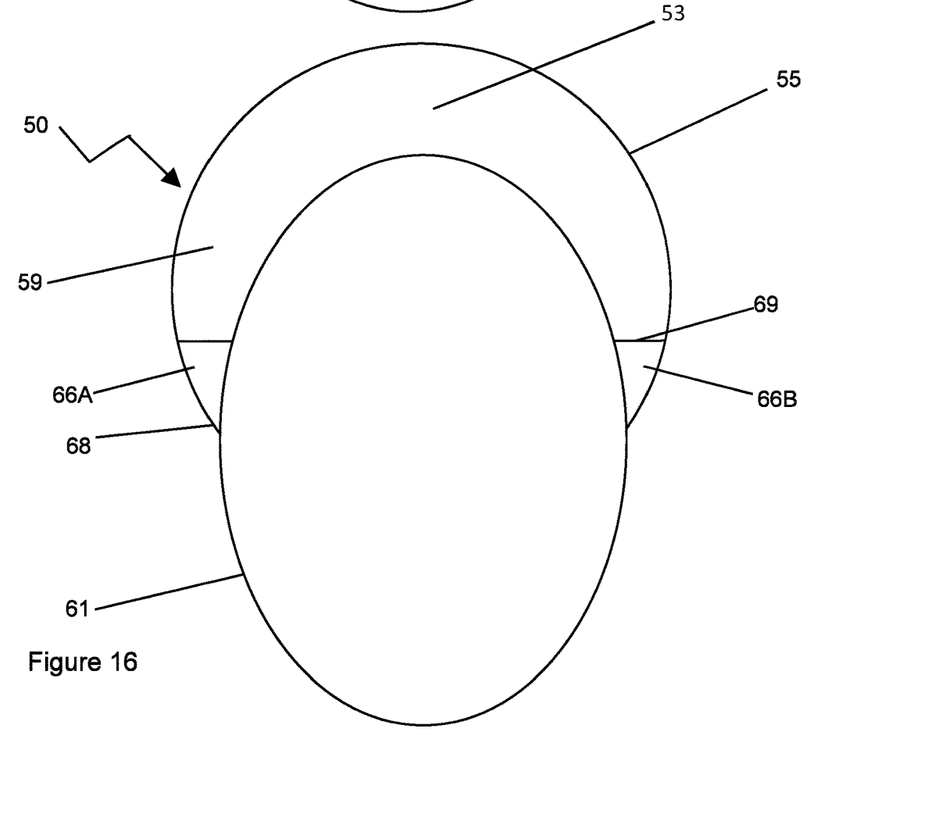
FIG. 16 shows the rear view of the stoma shown in FIG. 15, with the pouch partially visible.

The reverse side of stoma bag 50 is illustrated in FIG. 16 and shows impermeable backing layer 53 which prevents seepage of waste material contained by the device, for example absorbed into absorbent material 52. Backing layer 53 can be a thin film material (such as a thin film membrane, for example a polyurethane membrane) or could be a sheet of plastics material. Impermeable backing layer 53 and absorbent layer 52 together form flange extension member 59. The absorbent layer 32 can include particles of activated carbon or charcoal to assist with odour control. The pouch is attached to the flange extension member 59 in the same way as shown in FIGS. 4 and 6. Portions 66A and 66B of the pouch are visible in FIG. 16 as the pouch is positioned behind stoma bag 50. The pouch is attached to the flange at edge 68 and access to its interior provided by free edge 69.

Any modifications and/or variations to described embodiments that would be apparent to one of skill in art are hereby encompassed. Whilst the invention has been described herein with reference to certain specific embodiments and examples, it should be understood that the invention is not intended to be unduly limited to these specific embodiments or examples.

I claim:

1. A device for containing waste material leaking from a junction between a stoma and a stoma bag having a flange, said device comprising a flange extension member which comprises a layer of absorbent material, wherein said flange extension member circumferentially surrounds and extends beyond the stoma bag flange, wherein said flange extension member has a skin-facing side to face towards a user's skin and a non-skin-facing side to face away from a user's skin, and wherein a pouch for holding a spare stoma bag is formed within said flange extension member, wherein said pouch is located on the non-skin-facing side of the flange extension member.

2. The device as claimed in claim 1 wherein said flange extension member and said pouch are each formed from sheet material.

3. The device as claimed in claim 2 wherein said sheet material comprises a waterproof or impermeable backing layer.

4. The device as claimed in claim 1 wherein said flange extension member has adhesive at or close to its outer edge for attachment to the user's skin.

5. The device as claimed in claim 1 wherein the flange extension member is substantially circular and said pouch is shaped to match a segment thereof.

6. The device as claimed in claim 1 wherein the flange extension member is asymmetric and said pouch is shaped to match a segment thereof.

7. The device according to claim 1 wherein the layer of absorbent material comprises activated carbon or activated charcoal.

8. A stoma bag flange, said flange having an inner area for adhesion to the skin around a stoma, and a flange extension member which comprises a layer of absorbent material, wherein said flange extension member circumferentially surrounds and extends beyond the flange inner area, wherein said flange extension member has a skin-facing side to face towards a user's skin and a non-skin-facing side to face away from a user's skin, and wherein a pouch for holding a spare stoma bag is formed within said flange extension member, wherein said pouch is located on the non-skin-facing side of the flange extension member.

9. The flange as claimed in claim 8, wherein said flange extension member and said pouch are each formed from sheet material.

10. The flange as claimed in claim 8 wherein said flange extension member has adhesive at or close to its outer edge for attachment to the user's skin.

11. The flange as claimed in claim 8 wherein said sheet material comprises a waterproof or impermeable backing layer.

12. The flange as claimed in claim 8 wherein the flange extension member is substantially circular and said pouch is shaped to match a segment thereof.

13. The flange as claimed in claim 8 wherein the flange extension member is asymmetric and said pouch is shaped to match a segment thereof.

14. The flange as claimed in claim 8 wherein the flange extension member extends beyond the flange inner area by at least 2 cm.

15. The flange according to claim 8 wherein the layer of absorbent material is configured to draw any waste material outwardly from the stoma.

16. A stoma bag having stoma bag flange with an aperture for location around a stoma, and wherein a flange extension member comprising a layer of absorbent material circumferentially surrounds and extends beyond the stoma bag flange, wherein said flange extension member has a skin-facing side to face towards a user's skin and a non-skin-facing side to face away from a user's skin, and wherein a pouch for holding a spare stoma bag is formed within said flange extension member, wherein said pouch is located on the non-skin-facing side of the flange extension member.

17. The stoma bag as claimed in claim 16, wherein said flange extension member and said pouch are each formed from sheet material.

18. The stoma bag as claimed in claim 16 wherein said sheet material comprises a waterproof or impermeable backing layer.

19. The stoma bag as claimed in claim 16 wherein said flange extension member has adhesive at or close to its outer edge for attachment to the user's skin.

20. The stoma bag as claimed in claim 16 wherein the flange extension member is substantially circular.

21. The stoma bag as claimed in claim 16 wherein the flange extension member is asymmetric.

22. The stoma bag as claimed in claim 16 wherein the flange extension member extends beyond the stoma bag flange by at least 2 cm.

23. The stoma bag as claimed in claim 16 further comprising a spare stoma bag located in the pouch.

* * * * *